US00PP11597P

United States Patent [19]

Dümmen

[11] Patent Number: Plant 11,597

[45] Date of Patent: Oct. 24, 2000

[54] GUINEA IMPATIENS PLANT NAMED 'DUEPETPINKEYE'

[75] Inventor: Marga Dümmen, Rheinberg, Germany

[73] Assignee: Dümmen Jungpflanzenkulturen, Rheinberg-Eversael, Germany

[21] Appl. No.: 09/233,130

[22] Filed: Jan. 19, 1999

[51] Int. Cl.[7] ..... A01H 5/00

[52] U.S. Cl. ..... Plt./318

[58] Field of Search ..... Plt./318

[56] References Cited

U.S. PATENT DOCUMENTS

P.P. 10,255 2/1998 Neeman ..... Plt./318

P.P. 10,867 4/1999 Bull ..... Plt./318

*Primary Examiner*—Howard J. Locker

*Assistant Examiner*—Kent L. Bell

*Attorney, Agent, or Firm*—C. A. Whealy

[57] ABSTRACT

A new and distinct cultivar of New Guinea Impatiens plant named 'Duepetpinkeye', characterized by its rounded flowers that are white with a dark red "eye" zone; freely flowering; freely branching plant habit; and leaves that have dark green upper surfaces, dark wine red lower surfaces, and dark wine red venation.

1 Drawing Sheet

BACKGROUND OF THE INVENTION

The present invention relates to a new and distinct cultivar of New Guinea Impatiens plant, botanically known as *Impatiens hawkeri,* and hereinafter referred to by the name 'Duepetpinkeye'. The new cultivar is marketed under the name Improved Petticoat Pink Eye.

The new cultivar is a product of a planned breeding program conducted by the Inventor in Rheinberg, Germany. The objective of the breeding program is to develop New Guinea Impatiens that are freely branching; early flowering; and that have desirable flower and leaf colors.

The new cultivar originated from a cross made by the Inventor of the *Impatiens hawkeri* proprietary selection identified as K22 as the female, or seed, parent with the *Impatiens hawkeri* proprietary selection identified as D87 as the male, or pollen, parent.

The cultivar 'Duepetpinkeye' was discovered and selected by the Inventor as a single flowering plant within the progeny of the stated cross in a controlled environment in Rheinberg, Germany.

Asexual reproduction of the new cultivar by terminal cuttings taken at Rheinberg, Germany, has shown that the unique features of this new cultivar are stable and reproduced true to type in successive generations of asexual reproduction.

BRIEF SUMMARY OF THE INVENTION

The following traits have been repeatedly observed and are determined to be the unique characteristics of 'Duepetpinkeye'. These characteristics in combination distinguish 'Duepetpinkeye' as a new and distinct cultivar:

1. Rounded flowers that are white with a dark red "eye" zone and about 5.7 cm in diameter.
2. Freely flowering.
3. Freely branching plant habit.
4. Leaves that have dark green upper surfaces, dark wine red lower surfaces, and dark wine red venation.

Compared to plants of the female parent, plants of the new cultivar differ in flower color and are more freely branching.

Compared to plants of the male parent, plants of the new cultivar have darker green foliage.

The new cultivar can be compared to the commercial cultivar 'Dueripinkeye' (disclosed in U.S. Plant Pat. No. 11,320). However, plants of the new cultivar are more freely branching and have a less intense "eye" than plants of the cultivar Dueripinkeye.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph may differ slightly from the color values cited in the Detailed Botanical Description which accurately describe the actual colors of the new cultivar. The photograph comprises a side perspective view of a typical plant of 'Duepetpinkeye' grown in a 11-cm container.

DETAILED BOTANICAL DESCRIPTION

Plants of 'Duepetpinkeye' have not been observed under all possible environmental conditions. The phenotype may vary somewhat with variations in environment such as temperature, daylength and light intensity, without, however, any variance in genotype. The following observations and measurements describe plants grown in 11-cm containers during the fall in Rheinberg, Germany, under commercial practice in a glass-covered greenhouse with day and night temperatures about 18° C. and light levels about 4,500 lux.

In the following description, color references are made to The Royal Horticultural Society Colour Chart except where general terms of ordinary dictionary significance are used.

Botanical classification: *Impatiens hawkeri* cultivar 'Duepetpinkeye'.

Parentage:

*Female, or seed, parent.*—Proprietary selection of *Impatiens hawkeri* identified as K22.

*Male, or pollen, parent.*—Proprietary selection of *Impatiens hawkeri* identified as D87.

Propagation:

*Type cutting.*—Terminal cuttings.

*Time to initiate roots.*—Summer: About 10 days at 22° C. Winter: About 12 days at 22° C.

*Time to develop roots.*—Summer: About 21 days at 22° C. Winter: About 24 days at 22° C.

*Rooting habit.*—Freely branching, thick.

Plant description:

*General appearance.*—Rounded; dense; very freely and basally branching; upright and spreading; moderate growth rate and vigor; most suitable for 11-cm pots. About 15 to 16 weeks are required to produce a finished 11-cm container from an unrooted cutting.

*Plant height.*—About 15.75 cm from soil level to top of plant plane.

*Lateral branches.*—Length: About 7 cm. Diameter: About 5.3 mm. Internode length: About 2 cm. Color: 53B.

*Foliage description.*—Quantity of leaves per lateral branch: About 9. Shape: Elliptic with apiculate apex and attenuate base. Length: About 6.7 cm. Width: About 2.9 cm. Texture: Rough and leathery. Margin: Serrulate with ciliation. Color: Young foliage, upper surface: 139A. Young foliage, lower surface: 131A to 59A. Mature foliage, upper surface: 131A. Mature foliage, lower surface: 59A. Veins, upper surface: 59A. Veins, lower surface: 59A. Petiole: Length: About 1.4 cm. Diameter: About 2.8 mm. Color: 59A.

Flower description:

*Flowering habit.*—Freely flowering.

*Natural flowering season.*—Year-round. Early flowering, plants flower about 6 or 7 weeks after planting. Flowering intermittent.

*Rate of flower opening.*—About 3 days.

*Flower longevity.*—About 14 to 20 days.

*Flowers borne.*—Flower buds develop in apical leaf axils. Open flowers are displayed about the foliage.

*Quantity of inflorescences.*—Extremely floriferous: usually about 125 buds and flowers per plant.

*Flower shape.*—Rounded.

*Flower diameter.*—About 5.7 cm.

*Flower depth.*—About 3.5 mm.

*Petals.*—Shape: Reniform/cordate with emarginate apex and acute base. Quantity, arrangement: Five petals overlapping. Aspect: Flat. Length: About 2.5 cm. Width: About 3.15 cm. Texture: Smooth, satiny, glossy, and glabrous. Margin: Entire. Color: When opening, upper surface: Close to white, 155D, with dark red, 53A, "eye" zone. When opening, lower surface: White, 155C, with dark red, 53A, "eye" zone. Fully opened, upper surface: White, 155D, with dark red, 53A, "eye" zone and center stripe on uppermost petal. White areas become light pink, 73D, with age. When opening, lower surface: White, 155C, with dark red, 53A, "eye" zone and center stripe on uppermost petal.

*Peduncle.*—Angle: Erect. Length: About 4.5 cm. Color: 53A.

*Flower bud.*—Shape: Ovoid with spur. Length: About 1.5 cm. Diameter: About 9.2 mm. Color: 53A.

*Spur.*—Shape: Needle-shaped, curved at end. Length: About 4.8 cm. Color: 60A.

*Reproductive organs.*—Androecium: Stamen number: 5. Anther shape: Oval. Anther size: About 4.2 mm. Anther Color: 62C. Pollen color: 155A. Amount of pollen: Abundant. Gynoecium: Pistil length: About 4.2 mm. Stigma color: 60A. Style color: 60A. Ovary color: 59B.

Disease resistance: Resistance to known pathogens of New Guinea Impatiens has not been observed.

Seed development: Seed production has not been observed.

It is claimed:

1. A new and distinct cultivar of New Guinea Impatiens plant named 'Duepetpinkeye', as illustrated and described.

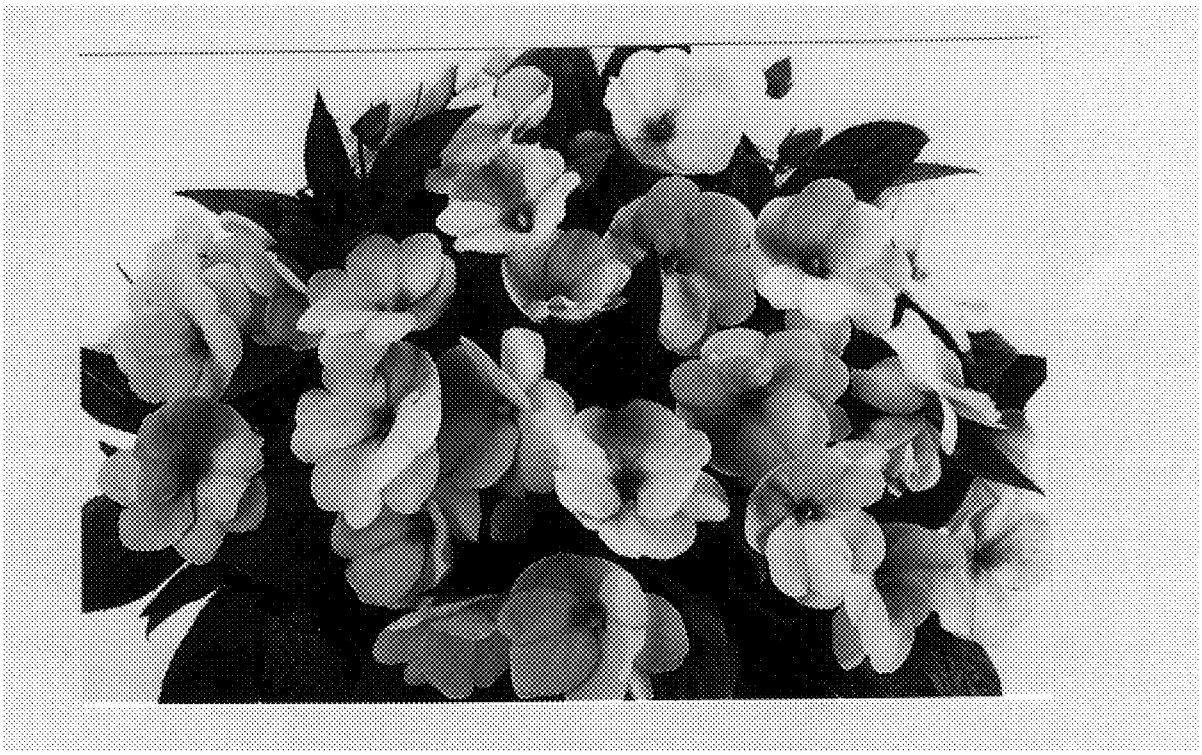

* * * * *